US007285091B2

(12) United States Patent
Blodgett et al.

(10) Patent No.: US 7,285,091 B2
(45) Date of Patent: Oct. 23, 2007

(54) ASSESSMENT OF TOOTH STRUCTURE USING LASER BASED ULTRASONICS

(75) Inventors: David W. Blodgett, Ellicott City, MD (US); Kevin C. Baldwin, Columbia, MD (US); Donald D. Duncan, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 303 days.

(21) Appl. No.: 10/250,882

(22) PCT Filed: Jan. 10, 2002

(86) PCT No.: PCT/US02/01138

§ 371 (c)(1),
(2), (4) Date: Jul. 10, 2003

(87) PCT Pub. No.: WO02/054948

PCT Pub. Date: Jul. 18, 2002

(65) Prior Publication Data

US 2004/0077949 A1    Apr. 22, 2004

Related U.S. Application Data

(60) Provisional application No. 60/261,090, filed on Jan. 11, 2001.

(51) Int. Cl.
*A61B 8/00* (2006.01)
*A61C 5/00* (2006.01)
(52) U.S. Cl. .................. 600/437; 600/438; 433/215
(58) Field of Classification Search ........ 600/437–438, 600/443–447, 407, 473, 476; 433/2, 24, 433/29, 40, 68, 140, 215; 356/237.1, 239.7, 356/900–903; 73/601–603, 643
See application file for complete search history.

(56) References Cited

U.S. PATENT DOCUMENTS

| | | | |
|---|---|---|---|
| 4,255,971 A | * | 3/1981 | Rosencwaig ................. 73/606 |
| 4,554,836 A | * | 11/1985 | Rudd ............................ 73/657 |
| 4,571,080 A | * | 2/1986 | Papuchon et al. ........... 356/477 |
| 4,611,288 A | * | 9/1986 | Duret et al. ................. 700/163 |
| 4,834,111 A | * | 5/1989 | Khanna et al. .............. 600/587 |
| 5,257,544 A | * | 11/1993 | Khuri-Yakub et al. ........ 73/579 |

(Continued)

OTHER PUBLICATIONS

Altshuler et al "Tissue-differentiating and Laser-control Process for Treating Hard Dental Tissue by Laser Pulses" WO 95/27446 Oct. 19, 1995.*

(Continued)

*Primary Examiner*—Francis J. Jaworski
(74) *Attorney, Agent, or Firm*—Francis A. Cooch (57) ABSTRACT

A means of assessing the internal structure of teeth based upon use of high frequency, highly localized ultrasound (acoustic waves) generated by a short laser pulse is presented. In contrast to traditional contact transducer methods, laser-generated ultrasound is non-contact and non-destructive in nature and requires no special tooth surface preparation. Optical interferometric detection of ultrasound provides a complementary non-destructive, non-contact means for obtaining data with a very small detection footprint. The combination of laser-generated ultrasound and optical interferometric detection allows for in-vivo diagnostics of tooth health that is sensitive to the enamel/dentin, dentin/pulp, and dentin/cementum interfaces as well as a region of dead tracts in the dentin within a tooth.

23 Claims, 7 Drawing Sheets

U.S. PATENT DOCUMENTS

| | | | |
|---|---|---|---|
| 5,570,182 A * | 10/1996 | Nathel et al. | 356/511 |
| 5,718,226 A * | 2/1998 | Riza | 600/437 |
| 5,720,894 A * | 2/1998 | Neev et al. | 216/65 |
| 6,041,020 A | 3/2000 | Caron et al. | |
| 6,402,707 B1 * | 6/2002 | Ernst | 600/590 |
| 6,532,821 B2 * | 3/2003 | Lamouche et al. | 73/643 |
| 6,584,341 B1 * | 6/2003 | Mandelis et al. | 600/476 |
| 6,605,080 B1 * | 8/2003 | Altshuler et al. | 606/3 |
| 6,608,684 B1 * | 8/2003 | Gelikonov et al. | 356/479 |
| 6,997,883 B1 * | 2/2006 | Hahn | 600/560 |

OTHER PUBLICATIONS

Fighting Tooth Decay, Help Is on the Way, http://www.intelihealth.com: Mar. 29, 2001.

Laser Ultrasonic Techniques for Assessment of Tooth Structure, in Laser Tissue Interaction XI: Photo-Chemical, Photothermal & Photomechanical; by DW Blodget. et al. Jan. 22, 2000.

* cited by examiner

ASSESSMENT OF TOOTH STRUCTURE USING LASER BASED ULTRASONICS

CROSS REFERENCE TO RELATED APPLICATIONS

This application is a 371 of PCT/USO2/01138 filed Jan. 10, 2002 which claims the benefit of U.S. Provisional Patent Application Ser. No. 60/261,090, filed Jan. 11, 2001 entitled "Assessment of Tooth Structure Using Laser Based Ultrasonics".

FIELD OF THE INVENTION

The present invention is an apparatus and a method related to using laser based ultrasonics to aid in the assessment of tooth structure.

BACKGROUND

The benefits of ultrasonics to examining soft tissue structures, particularly the abdominal region, brain, and eyes have long been known. In these applications, typically one or more acoustic contact transducers is used to generate and detect acoustic waves in the structure. These procedures are simplified, at least for examination of teeth, with the relatively large dimensions being examined, slower acoustic wave velocity (allowing lower frequency acoustic waves to be used for equivalent acoustic wavelengths), and readily available acoustic coupling material for the transducer to the soft tissue. (Soft tissue, unlike hard tooth enamel and dentin, is largely composed of water, making water a very efficient coupling material.)

Attempts to adapt conventional ultrasonic techniques to examination of internal structure of a tooth have met with little success. One major obstacle is identifying a suitable couplant for the transducer to the tooth for in-vivo measurements. Without proper coupling, transferring acoustic energy into the tooth is difficult. Early investigators attempted using water, as with soft tissue structures, but results were not convincing.

The coupling problem was overcome by replacing water with mercury. Although providing superior coupling efficiency, mercury is not suitable for clinical applications due to its toxicity.

Another solution to overcome the coupling difficulty was using a small aluminum buffer rod to transfer the acoustic energy from the contact transducer to the tooth. An estimated transmission efficiency of almost 87% was achieved using this technique, compared to only 5% using water. However, a significant limitation of this system was coupling the aluminum buffer rod with the tooth surface. To ensure proper coupling of the acoustic energy to the tooth, a flat spot had to be ground on the tooth surface, making this technique unsuitable for clinical applications. In addition, the relatively large contact area (3.2 mm diameter) limited the spatial resolution of the probe. For assessing anomalies in a tooth, such as poor bonding or voids between the restorative material and the dentin, a detection footprint smaller than the anomaly itself is required.

One method of increasing spatial resolution of a contact transducer is to use a spherical transducer that focuses abeam onto a sample (tooth) surface. This method forms the basis of the acoustic microscope, the acoustic equivalent of an optical microscope. This technique was used to study unblemished and demineralized enamel from extracted human teeth, using water as a couplant. The inspection depths were thus limited to approximately 0.5 to 1.5 mm.

More recently, the increased spatial resolution of the acoustic microscope was used to detect small caries lesions in sections of human enamel. However, as with previous work, special polishing of the tooth samples was required, making the technique ill-suited for clinical applications.

What is needed is a tooth structure assessment system achievable in-vivo operation that combines superior coupling efficiency, a small detection footprint size, and no special tooth surface preparation.

SUMMARY

To help overcome previous difficulties in coupling efficiency, detection footprint size, and special surface preparation, the present invention utilizes laser-generated ultrasound techniques. Laser-generated ultrasound uses a short-pulse laser, in place of a contact transducer, to generate high frequency (broad-band) ultrasound in a material. Due to the absorption of pulse energy at or near the surface of the specimen, temperature gradients are established within the material, producing a rapidly changing strain field. This strain field, in turn, radiates energy as elastic (ultrasonic) waves. At low pulse energies, this is an entirely thermo-elastic process resulting in no damage to the material under test. An advantage of this technique over the previous methods is that no special surface preparation of the tooth is required. In addition, by focusing the laser beam onto the surface of the tooth, a very small contact (generation) area can be achieved. Spot size diameters on the order of tens of microns are routinely achieved.

Both enamel and dentin have strong absorption bands in the longwave infrared (IR) spectrum (9 to 11 μm). These optical properties have already led to applications for the carbon-dioxide ($CO_2$) laser in fusing enamel, dentin, and apatite. Fusion inhibits subsequent lesion progression and markedly improves bonding strength of a composite resin to dentin. For illustration purposes with respect to the present invention, a short pulse $CO_2$ laser has been used to generate acoustic waves in an extracted human incisor. In some instances, other lasers, such as, for instance, a pulsed Nd:YAG laser may be used.

Optical detection of the ultrasound, such as by a laser vibrometer interferometer, provides a complementary technique for remote sensing of ultrasonic waves. Techniques based upon the sensing of the optical wavefront reflection from the tooth, such as Fabry-Perot interferometers, Mach-Zender interferometers, Michelson interferometers, photorefractive interferometers, optical feedback interferometry, and several other types of laser vibrometers, are well suited for diffusely reflecting surfaces. For purposes of illustration with respect to the disclosure herein, a laser vibrometer is described to detect acoustic wave arrivals.

One embodiment of the present invention is a method of assessing tooth structure using laser based ultrasonics. Ultrasonic acoustic waves are generated using a pulsed laser. The beam of the pulsed laser is focused onto a desired area on the surface of a tooth thereby creating ultrasonic acoustic waves within the bulk and along the surface of the tooth structure. These acoustic waves are optically detected using optical interferometric means. Finally, detected acoustic waveforms are processed to assess the internal or surface structure of the tooth.

Another embodiment of the present invention is an apparatus including a pulsed laser that generates a beam of ultrasonic acoustic waves. The beam is focused by a lens onto a desired area on the surface of a tooth creating ultrasonic acoustic waves within the bulk and along the surface of the tooth structure. Optical interferometric detection means optically detect the acoustic waves generated within the tooth structure and an oscilloscope processes the detected acoustic waveforms to assess the internal structure of the tooth. The short pulse laser operates in a region of absorption for the tooth structure.

In another embodiment, a thin film or coating can be placed on the tooth surface and the short pulse laser then operates in a region of absorption for the thin film or coating.

DETAILED DESCRIPTION

The generation and detection of ultrasonic waves provides a method for characterizing the bulk and surface properties of a material by interrogating a specimen with high frequency acoustic waves. Up to three bulk acoustic waves can propagate in a material, each with its own characteristic velocity. As an ultrasonic wave propagates, the amplitude decreases due to geometrical spreading, attenuation from absorption, and scattering from discontinuities. Measurement of wave speeds, attenuation, and scattering provide the information needed to quantify the bulk internal and surface properties of the material. In this analysis, we are interested in the interaction of the acoustic waves at the interfaces between the dental hard and soft tissues.

The propagation of elastic plane waves in an anisotropic material is described using Christoffel's equation by:

$$|C_{ijkl} l_j l_l - \rho v^2 \delta_{ik}| = 0.$$

This equation provides an analytic relation between the phase velocity, v, of the elastic waves and the elastic moduli, $C_{ijkl}$. The direction cosines are specified by $l_i$ (with i=1, 2, or 3), $\rho$ is the material density, and $\delta_{ik}$ is the Kronecker delta function.

Figure 1:
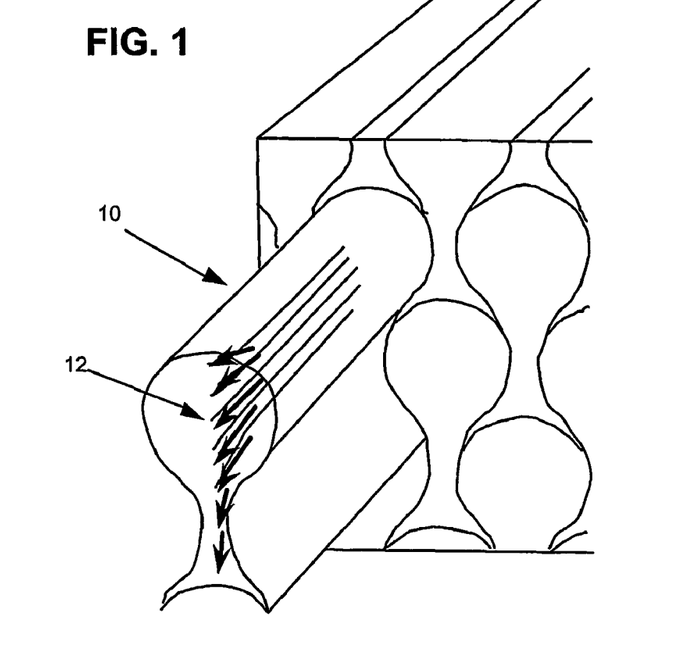
FIG. 1 illustrates the internal structure of tooth enamel.

The anisotropic nature of dental hard tissue is well-documented. Dental enamel, the hard protective substance covering the crown of the tooth, is the hardest biologic tissue in the body to resist fractures during mastication (chewing). Enamel is composed of about 96% inorganic mineral in the form of hydroxyapatite and 4% water and organic matter. Hydroxyapatite is a crystalline calcium phosphate that is also found in bone, dentin, and cementum. As illustrated in FIG. 1, enamel is composed of rods 10 that extend from their origin at the dentino-enamel junction to the outer surface of the tooth. The rod itself resembles a keyhole in shape, allowing individual rods to form a strong interlocking structure. The head of the rod measures about 5 µm across while the tail is only about 1 µm. Each rod is filled with crystals, whose orientation 12 varies along the rod. At the head of the rod, these crystals are approximately parallel to the rod axis while near the tail of the rod, the crystals are oriented almost perpendicular to the rod axis. Variations in the elastic properties of enamel are quantified by measuring the Rayleigh velocity as a function orientation with the enamel rods with an acoustic microscope. It was found that the Rayleigh velocity varied by almost 5% in these measurements. More recently, a three-dimensional finite element model was developed for the prismatic nature of enamel that predicted stiffness both along and across the rods and found that Young's modulus varies dramatically both with direction and volumetric fraction. Specifically, the deviation in Young's modulus is estimated at nearly ±10% parallel and ±60% perpendicular to the orientation of crystals.

Figure 2:
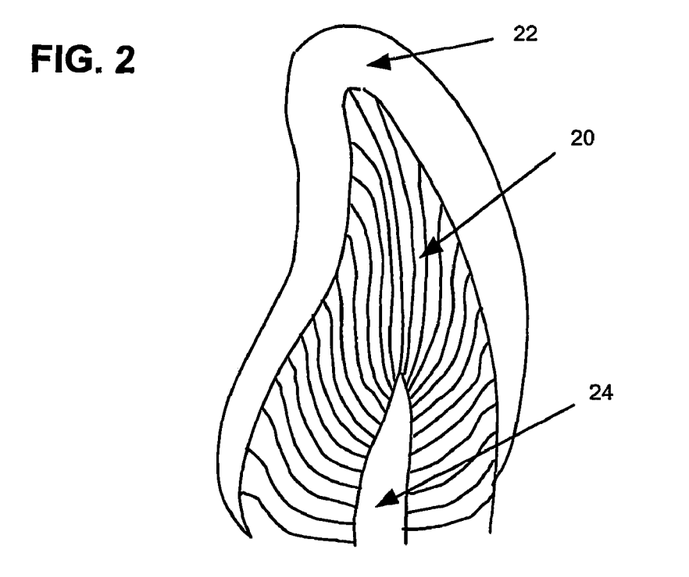
FIG. 2 illustrates the internal structure of tooth dentin.

Referring to FIG. 2, dentin 20 is the hard tissue that constitutes the body of a tooth. Unlike enamel, which is almost white in color, dentin appears almost yellowish. Dentin is a living tissue that is not normally exposed to the oral environment. Like bone, dentin is composed primarily of an organic matrix of collagen fibers (20%), inorganic hydroxyapatite crystals (70%), and about 10% water. With 20% less mineral than enamel 22, dentin 20 is softer and slightly elastic. Dentin 20 itself is classified as primary, secondary, and tertiary on the basis of the time of its development and the histologic (microscopic) characteristics of the tissue. Primary dentin is the major component of the crown and root while secondary dentin forms only after tooth eruption (i.e. when the teeth begin to function) and borders the pulp. Finally, tertiary or reparative dentin occurs in response to the presence of a trauma to the pulp 24. The structure of dentin 20 is composed of S-shaped tubules that run from the dentino-enamel junction to the dentino-pulp junction. Each of these tubules is about 1-3 µm in diameter and surrounded by a matrix of needle-shaped, hydroxyapatite crystals in a protein matrix of composed mostly of callogen.

The third component of a tooth is the pulp 24, which is the soft connective tissue located in the central portion of each tooth. It is composed of both a crown (coronal part) and root (radicular part). Pulp 24 contains specialized connective tissue composed of thin-walled blood vessels, nerves, and nerve endings enclosed within the dentin 20.

To simplify analysis, enamel, dentin, and pulp are characterized as elastically isotropic. For isotropic materials, only two bulk waves need be considered, longitudinal and shear. It can be shown through Christoffel's equation that the velocity of these two wave's is given by:

$$v_{long} = \sqrt{\frac{C_{11}}{\rho}} = \sqrt{\frac{E}{\rho}} \text{ and } v_{shear} = \sqrt{\frac{C_{44}}{\rho}} = \sqrt{\frac{\mu}{\rho}}.$$

where E is the elastic modulus and μ is the shear modulus. The acoustic velocities and density for the various components of a tooth are listed in Table 1. When assessing any multi-phase structure, such as a tooth, both the acoustic velocity and acoustic impedance of each layer must be considered. The acoustic impedance, Z, is defined as:

$$Z = \sqrt{E\rho} = \rho v_{long}.$$

When an acoustic wave travels from one medium to another (i.e. from the enamel to the dentin), a portion of the wave is reflected and the remaining portion is transmitted (assuming no other losses). The intensity of the reflected acoustic radiation, $I_r$, assuming plane wave propagation, at the interface between two different mediums with acoustic impedances of $Z_1$ and $Z_2$, is given by:

$$I_r = \left(\frac{Z_2 - Z_1}{Z_2 + Z_1}\right)^2 I_i = \Gamma I_i,$$

where $\Gamma$ is the reflection coefficient and $I_i$ is the intensity of the incident radiation. Due to conservation of energy, the intensity of the transmitted acoustic radiation, $I_t$, is:

$$I_t = I_i - I_r.$$

Knowledge of the relative reflected and transmitted intensities at each material interface in a tooth structure aids in the interpretation of the final ultrasonic waveform.

Efficient ultrasound generation depends upon the material's absorption characteristics at the optical wavelength of the pulsed laser. Enamel and dentin have a strong absorption in the 9-11 μm region due to the phosphate in the carbonated hydroxyapatite (CAP). Absorption coefficients of 5500, 8000, 1125, and 825 $cm^{-1}$ at 9.3, 9.6, 10.3, and 10.6 μm, respectively have been determined. These correspond to absorption depths between 1.25 and 12 μm.

Figure 3A:
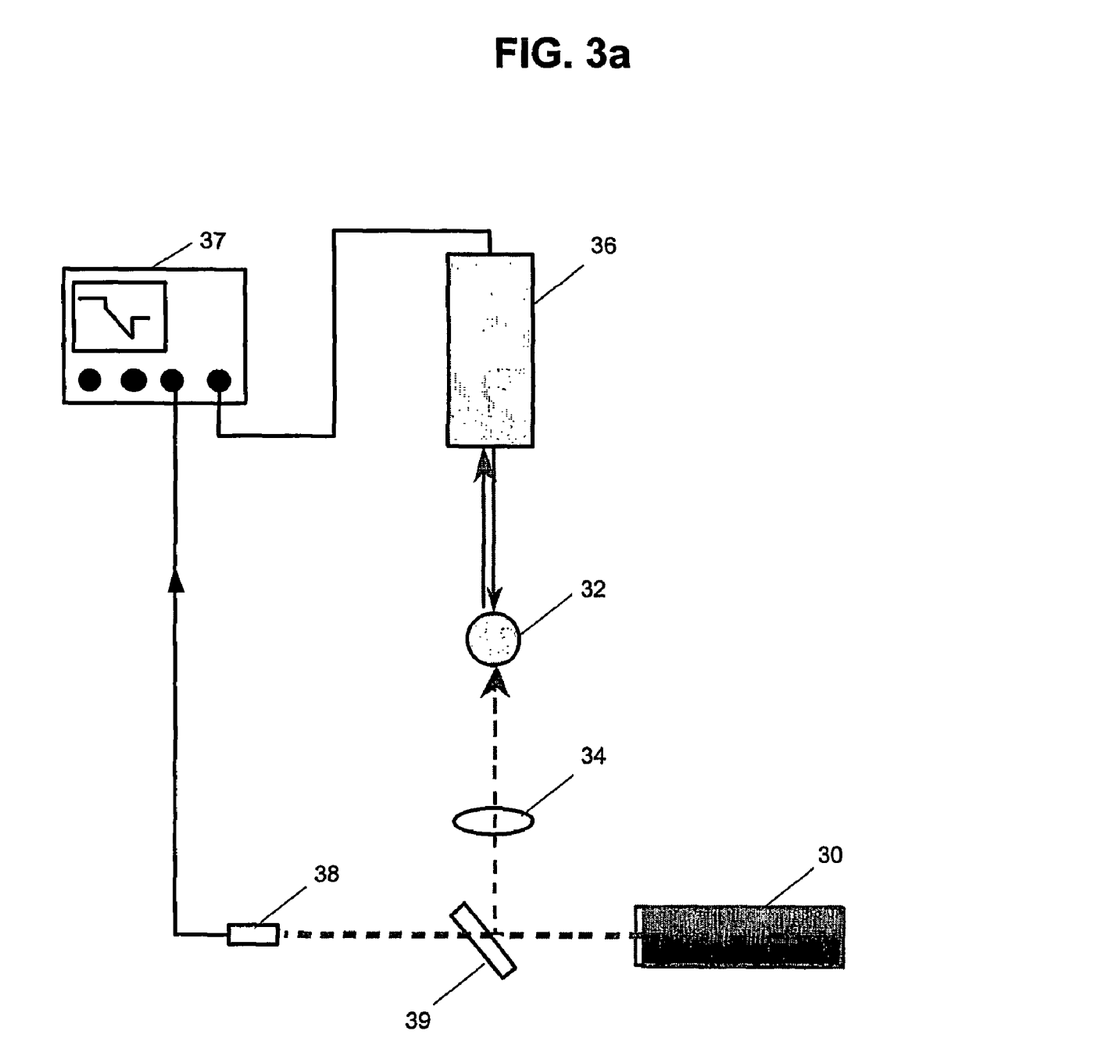
FIG. 3a illustrates a block diagram of components used in the present invention.

Referring now to FIG. 3a, a pulsed $CO_2$ laser 30 (10.6 μm with a 50 ns rise time) is used to generate acoustic waves in a human tooth 32. The pulsed laser 30 is focused to a spot size on the order of a few tens of microns on the tooth's surface via lens 34. The output power of the pulsed laser 30 is controlled using polarization optics to ensure non-destructive (thermo-elastic) acoustic wave generation. The short pulse laser operates in a region of absorption for the tooth structure. In another embodiment, a thin film or coating can be placed on the tooth surface and the short pulse laser then operates in a region of absorption for the thin film or coating.

Optical detection of the acoustic wave arrivals is accomplished using a laser vibrometer 36. The output signal from the vibrometer 36 is proportional to the surface displacement of the tooth 32. Ultrasound measurements can be taken in an epicentral configuration in which the source/laser 30 and receiver/vibrometer 36 are on opposite sides of the tooth 32. Alternatively, ultrasound measurements can be taken in an non-epicentral configuration in which the source/laser 30 and receiver/vibrometer 36 are on opposite sides of the tooth 32. In addition, ultrasound measurements can be taken wherein the source/laser 30 and receiver/vibrometer 36 are on the same side of the tooth 32.

The output of the vibrometer 36 is passed to a high-speed digitizing oscilloscope 37 for recording the ultrasonic event. The capture of the ultrasonic waveform is triggered by a high-speed photodetector, comprised of a photo-diode 38 and an output coupler 39, which sees a sampling of the output pulse of the pulsed laser 30. Sampling of the output laser pulse allows for very accurate time-of-flight measurements for the acoustic waves. In addition, multiple waveforms were averaged to improve the signal-to-noise ratio (SNR).

Figure 3B:
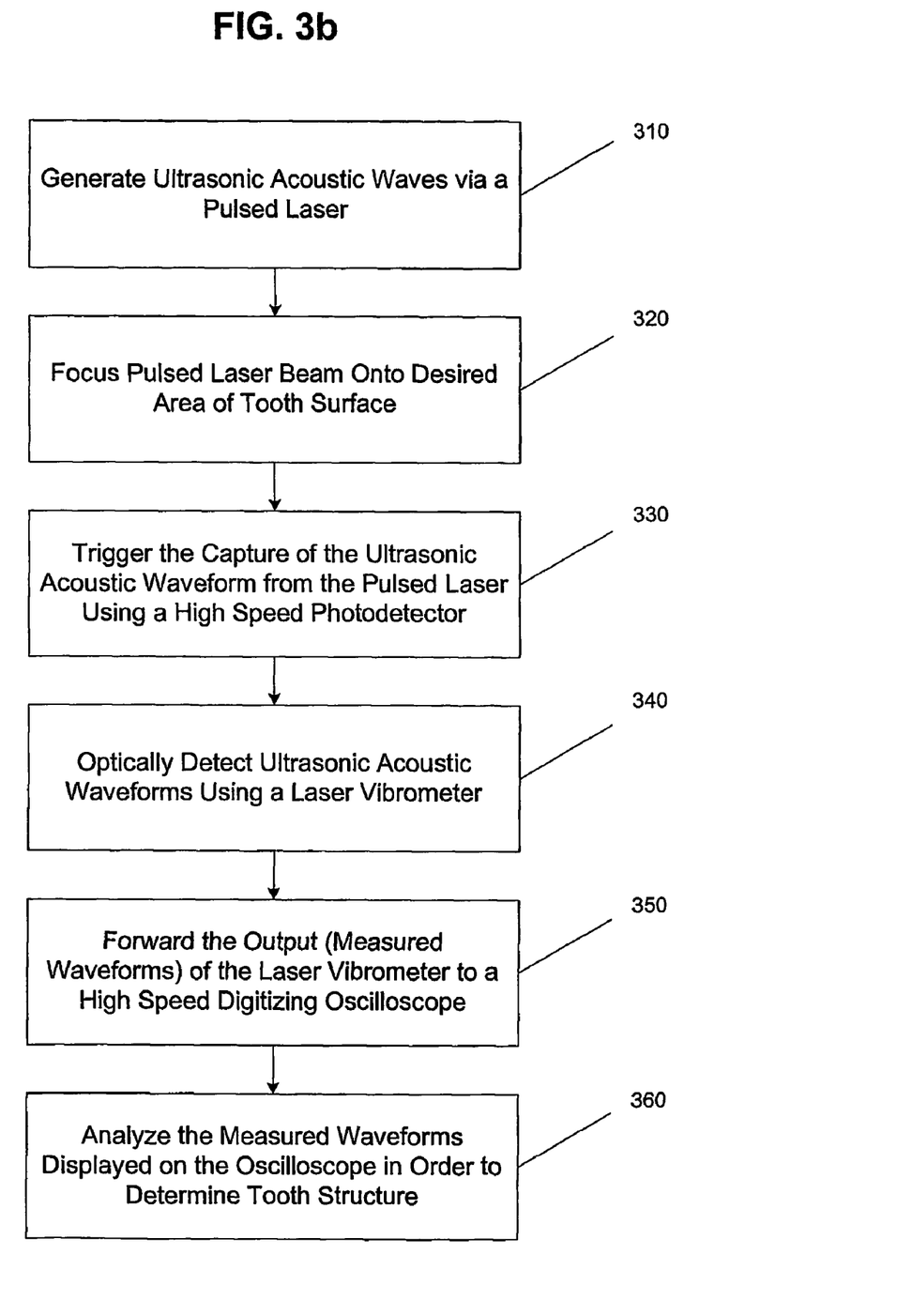
FIG. 3b is a flowchart illustrating the steps performed in the present invention.

FIG. 3b is a flowchart illustrating the steps performed in the present invention. Using the configuration described in FIG. 3a, ultrasonic acoustic waves are generated 310 via a pulsed laser. The beam of the pulsed laser is focused 320 onto the surface of a tooth at a desired area. The capture of the resulting acoustic waveforms within the tooth are triggered by a high speed photodetector that samples the output of the pulsed laser 330. A laser vibrometer is used to optically detect 340 acoustic waveforms generated within the tooth structure. The data recorded by the laser vibrometer is then forwarded to a high speed digitizing oscilloscope 350. The sampling of the pulsed laser provides the oscilloscope with very accurate time measurements with respect to the origination of the ultrasound beam. The detected acoustic waveforms are then processed, analyzed and displayed by the oscilloscope 360.

Processing of the results involves analysis of the peaks and valleys of the resulting waveforms versus time. Certain characteristics of a tooth's structure can be determined based on the arrival time and amplitude of the arrival of certain wave fronts. The processing is typically done by a processing device (computer) that can be programmed with the characteristics of normal tooth structure.

An advantage of the present invention is its ability to assess the health of the entire tooth structure. One application is to be able to resolve the interfaces of the various junctions that naturally occur in a tooth. Moreover, valuable diagnostic information can be determined by knowing, or at least estimating, the thicknesses of the various components that compromise a tooth. For example, there is a need to image the margins of a restoration for the detection of poor bonding or voids between the restorative material and the dentin. With conventional x-ray techniques, it is difficult to detect cracks and to visualize interfaces between hard media. This is due to the x-ray providing only a two-dimensional projection of the internal structure (i.e. a silhouette). In addition, a high resolution imaging modality is needed to detect tooth decay in its early stages. If decay can be detected early enough, the process can be monitored and interventional procedures, such as fluoride washes and controlled diet, can be initiated which can help the tooth to re-mineralize itself. Currently employed x-ray imaging is incapable of detecting decay at a stage early enough to avoid invasive cavity preparation followed by a restoration with a synthetic material. Laser ultrasonics can be used to detect early stages of decay both in the bulk and on the surface of the tooth. Other clinical applications include the visualization of periodontal defects, the localization of intraosseous lesions, and determining the degree of osseointegration between a dental implant and the surrounding bone.

To better illustrate the present invention, results of the use of the present invention on a tooth phantom and an extracted human incisor are presented and discussed.

Figure 4:
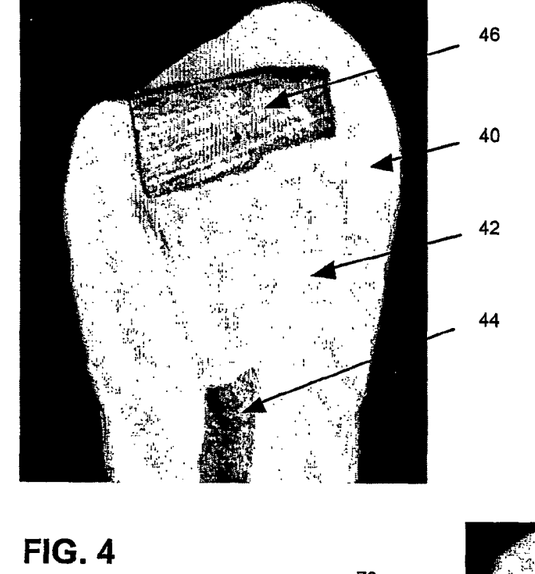
FIG. 4 illustrates a cross-section of an extracted human incisor showing the enamel, dentin, and pulp sections, and also an amalgam insert.

One means of better understanding the acoustic signature obtained from an actual tooth structure is to construct a tooth phantom made from acoustically similar materials. A cross section from an extracted human incisor is shown in FIG. 4.

The enamel 40, dentin 42, pulp 44, and an amalgam insert 46 are marked. To simplify construction, a separate tooth phantom was designed for four different acoustic "paths" through the tooth section. These paths include enamel, enamel/amalgam/enamel, enamel/dentin/enamel, and enamel/dentin/pulp/dentin/enamel.

Materials with similar acoustic velocities and impedances to the different components of a real tooth are listed in Table 1. Relatively good matches were found for enamel, pulp, and amalgam. Only dentin proved difficult to match. As shown in Table 1, tin has very similar acoustic velocities but much higher acoustic impedance. This larger impedance does not provide the desired interface characteristics between the different components of the tooth phantom. Borosilicate glass, on the other hand, has much faster acoustic velocities, but more comparable acoustic impedance. Since the purpose of this study was to better understand the interface properties between the different dental tissues, similarities in acoustic impedance was viewed as more important than acoustic velocities.

TABLE 1

| Layer | $V_{long}$ [mm/µs] | $V_{shear}$ [mm/µs] | Density $\rho$ [kg/m$^3$] | Acoustic Impedance Z [×10$^6$ kg/m$^2$s] |
|---|---|---|---|---|
| Enamel | 6.25 | 3.10 | 3000 | 18.8 |
| Aluminum | 6.30 | 3.10 | 2700 | 17.0 |
| Dentin | 3.80 | 1.90 | 2000 | 7.6 |
| Tin | 3.30 | 1.70 | 1740 | 24.2 |
| Borosilicate glass | 5.30 | 3.00 | 3570 | 18.9 |
| Pulp | 1.57 | 0.80 | 1000 | 1.57 |
| Teflon | 1.4 | | 2140 | 3.0 |
| Amalgam | 4.35 | 2.26 | 7750 | 33.7 |
| Copper | 4.70 | 2.30 | 9670 | 41.6 |

A comparison of the reflection coefficients between the interfaces of a real tooth and those of the tooth phantom are listed in Table 2.

TABLE 2

| Real Tooth | | Tooth Phantom | |
|---|---|---|---|
| Components | $\Gamma$ | Components | $\Gamma$ |
| enamel/amalgam/enamel | 0.081 | aluminum/copper/aluminum | 0.176 |
| enamel/dentin/enamel | 0.18 | aluminum/glass/aluminum | 0.026 |
| dentin/amalgam/dentin | 0.399 | glass/copper/glass | 0.296 |
| dentin/pulp/dentin | 0.432 | glass/teflon/glass | 0.369 |

Figure 5A:
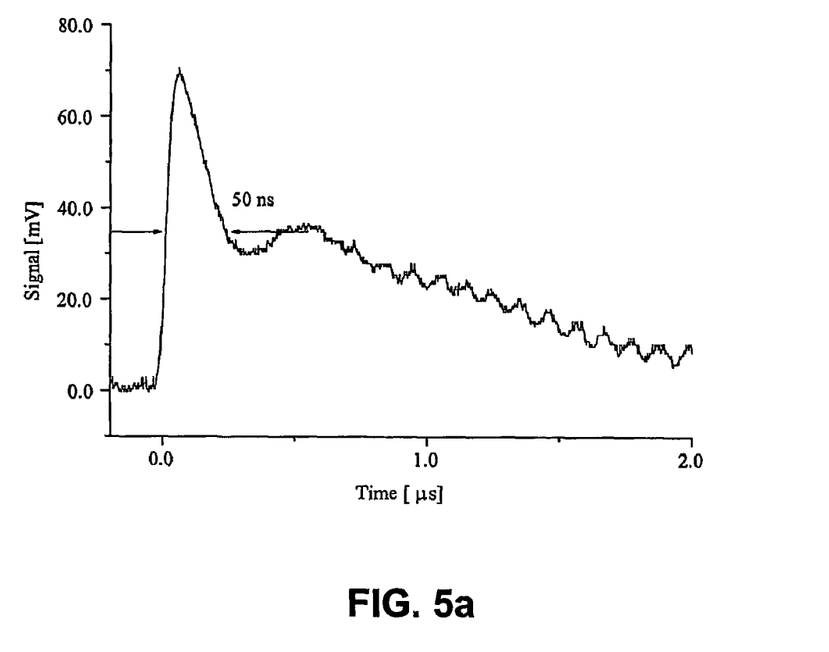
FIG. 5a illustrates a measured temporal profile of a $CO_2$ pulse laser.

A pulsed $CO_2$ laser is used to generate acoustic waves in the extracted human incisor. The measured temporal profile of a $CO_2$ laser, shown in FIG. 5a, indicates a pulse rise time of 50 ns. A noticeable feature of this pulse is the long tail (about 1.5 µs). Since only the rise of the initial pulse is responsible for high-frequency components of the ultrasonic waves, this tail did not effect the ultrasonic measurements.

Figure 5B:
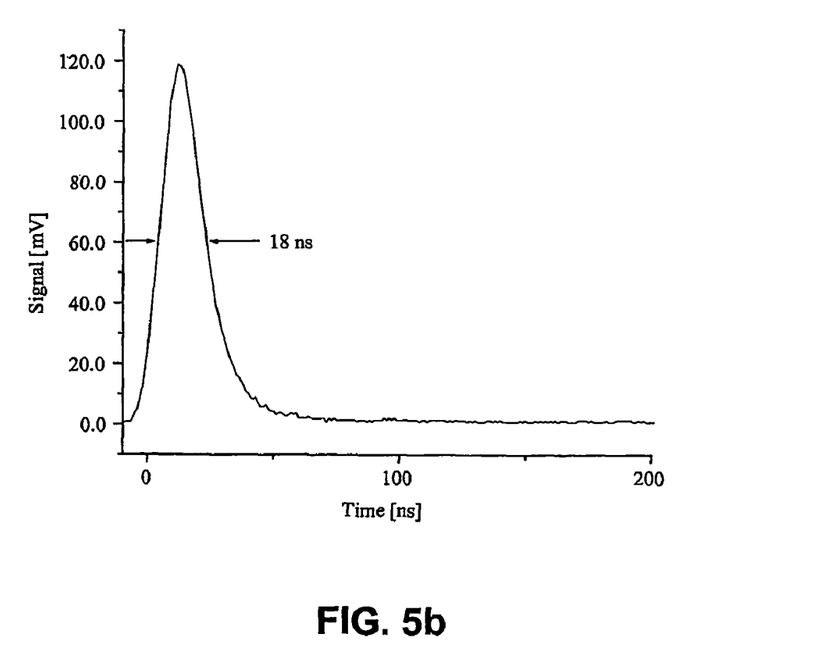
FIG. 5b illustrates a measured temporal profile of an Nd:YAG pulse laser.

Ultrasound generation in the tooth phantoms is accomplished using a pulsed Nd:YAG laser (18 ns pulse width). The measured temporal profile of a Nd:YAG pulse is illustrated in FIG. 5b. The poor absorption properties of aluminum in the tooth phantoms at 10.6 µm precluded the use of the $CO_2$ laser. In both cases, the pulsed lasers are focused to spot sizes on the order of a few ten's of microns and the output power of the pulsed lasers is controlled using polarization optics to ensure non-destructive (thermoelastic) acoustic wave generation.

A path-stabilized Michelson-type interferometer is used to detect the ultrasonic wave arrivals in the tooth phantoms. This type of interferometer is sensitive to sub-nanometer displacement amplitudes, typical for thermoelastically-generated ultrasound. Michelson interferometers are better suited to objects with specular reflections from the surface of the object. In each case, the front surface of the tooth phantom is polished to allow optimal operation of the interferometer. Since teeth do not provide a specular reflection, a different detection scheme is implemented. Optical detection schemes suited for diffusely reflecting surfaces include Fabry-Perot, Mach-Zender, photo-refractive, and optical feedback interferometers as well as various types of laser vibrometers. For these measurements, a commercially available laser vibrometer is used. As with the Michelson interferometer, this laser vibrometer has an output proportional to surface displacement.

Tooth Phantom Results

Figure 6A:
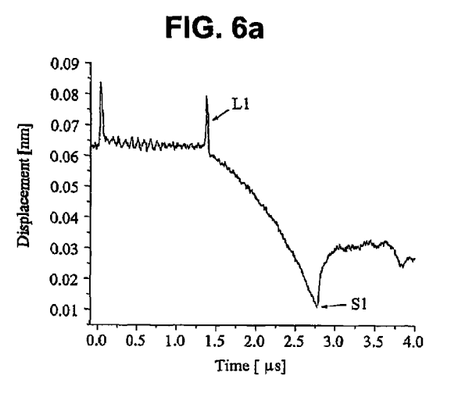
FIG. 6a illustrates an ultrasonic waveform for a tooth phantom taken in an enamel region.
Figure 6B:
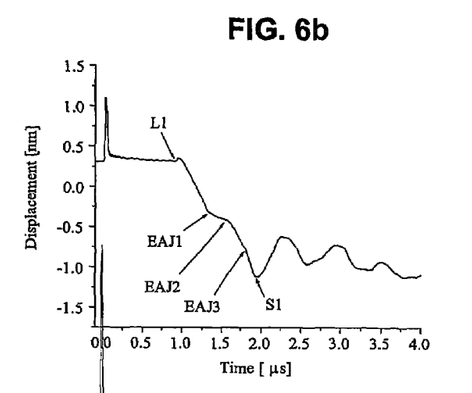
FIG. 6b illustrates an ultrasonic waveform for a tooth phantom taken in an enamel/amalgam/enamel region.
Figure 6C:
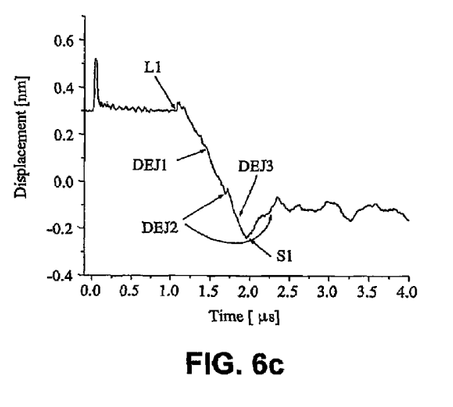
FIG. 6c illustrates an ultrasonic waveform for a tooth phantom taken in an enamel/dentin/enamel region.
Figure 6D:
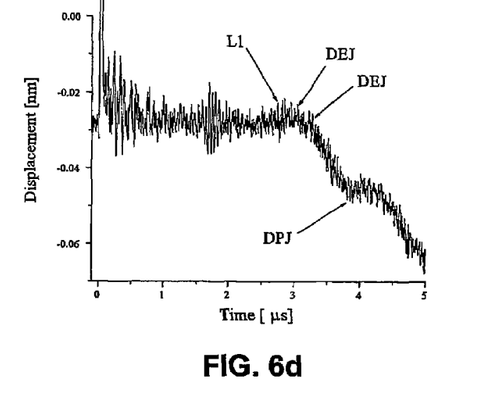
FIG. 6d illustrates an ultrasonic waveform for a tooth phantom taken in an enamel/dentin/pulp/dentin/enamel region.

FIG. 6a illustrates a measured thermoelastic ultrasonic waveform from a piece of aluminum (8.5 mm thick). This represents an ideal waveform through the enamel of a tooth if the enamel were truly isotropic. The first longitudinal wave (L1) and shear wave (S1) arrivals are marked. Scattered light from the pulsed laser denotes the beginning of the ultrasonic waveform. This initial laser pulse is visible on all of the tooth phantom waveforms. The aluminum waveform also provides a baseline for the other three tooth phantom waveforms (FIGS. 6b-d). Each of these waveforms is distinctly different due to reflections at the interfaces of the different layers of the tooth phantoms. Each waveform was averaged 100 times to improve SNR.

The measured waveform from the second tooth phantom illustrated in FIG. 6b simulates what would be found for a tooth with an amalgam restoration (filling). This phantom is composed of a 1.95 mm thick piece of copper (amalgam) sandwiched between two pieces of aluminum (enamel), 1.95 mm and 1.25 mm thick. The first longitudinal arrival time, $t_{L1}$, occurs at:

$$t_{L1} = \frac{d1_{aluminum}}{v_{aluminum}} + \frac{d_{copper}}{v_{copper}} + \frac{d2_{aluminum}}{v_{aluminum}}$$

$$= \frac{1.95 \text{ mm}}{6.3 \frac{\text{mm}}{\mu s}} + \frac{1.95 \text{ mm}}{4.7 \frac{\text{mm}}{\mu s}} + \frac{1.25 \text{ mm}}{6.3 \frac{\text{mm}}{\mu s}}$$

$$= 0.923 \text{ µs}.$$

The second acoustic wave arrival occurs when the longitudinal wave traverses the thin piece of aluminum (enamel) a second time after reflection at the enamel-amalgam junction (EAJ). This second arrival occurs at:

$$t_{EAJ1} = t_{L1} + \frac{d2_{aluminum}}{v_{aluminum}}$$

$$= 0.923 \text{ µs} + 0.397 \text{ µs}$$

$$= 1.32 \text{ µs}.$$

The next two acoustic wave arrivals result from additional traverses of the thicker piece of aluminum and the copper. In each case, the acoustic wave arrivals in the tooth phantom will be more pronounced than what would be expected for an actual tooth due to the larger reflection coefficient at the aluminum/copper junction (Γ=0.176 versus Γ=0.081). The first shear arrival is denoted by S1.

The ultrasonic waveform for the aluminum/glass/aluminum (enamel/dentin/enamel) tooth phantom is illustrated in FIG. 6c. The first longitudinal arrival (L1) is identified by the initiation of the positive slope in the waveform. As with the previous phantom, this arrival corresponds to a direct acoustic path for the longitudinal wave through the tooth phantom. In this tooth phantom, the first section of aluminum (enamel) is 1.95 mm thick, the glass (dentin) is 3.3 mm thick, and the final section of enamel is 1.25 mm thick. The second longitudinal arrival (DEJ1) occurs after the longitudinal wave traverses the thinner section of enamel (aluminum) a second time after reflection at the dentino-enamel (glass/aluminum) junction (DEJ). Subsequent longitudinal wave arrivals are also visible due to additional traverses of the thicker piece of enamel (aluminum) and dentin (glass) after reflections at the DEJ. The amplitude of each of these acoustic wave arrivals is smaller than in the previous tooth phantom due to the closer acoustic impedance match of the materials and subsequent smaller reflection coefficient (Γ=0.026). The DEJ would be more visible in an actual tooth due to the larger reflection coefficient (Γ=0.18).

The final ultrasonic waveform illustrated in FIG. 6d shows the enamel/dentin/pulp/dentin/enamel (aluminum/glass/teflon/glass/aluminum) tooth phantom. This tooth phantom is composed of 1 mm thick pieces of aluminum for the enamel, 3.5 mm thick pieces of glass for the dentin, and a 1.75 mm thick piece of teflon for the pulp. The lower SNR of this waveform is attributed to the increased complexity and thickness of this tooth phantom in comparison to the previous three. As before, the first longitudinal wave arrival (L1) corresponds to a single pass of the longitudinal wave through the phantom. The next two acoustic wave arrivals (DEJ) correspond to additional passes through the enamel (aluminum). As before, these reflections are very small due to the small reflection coefficient at the junction. The next acoustic wave arrival corresponds to a reflection at the dentin-pulp junction (DPJ). The amplitude of this reflection is far more pronounced due to the larger reflection coefficient.

Human Incisor Results

Figure 7:
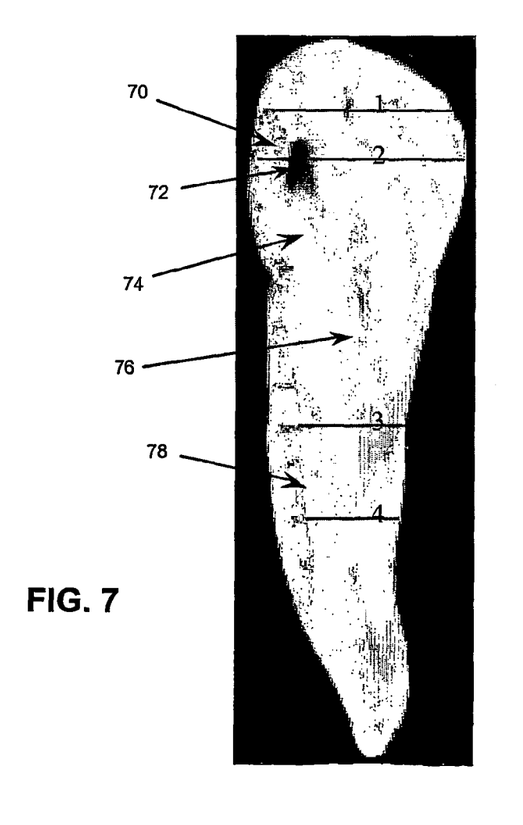
FIG. 7 illustrates a cross-section of an extracted human incisor.

Laser-based ultrasonic measurements were performed on an extracted human incisor. Prior to the measurements, the tooth was stored in a physiological saline to help preserve the mechanical properties of the dental tissue. After the measurements were completed, the incisor was cleaved along the propagation direction of the ultrasonic waves to determine the location of the internal interfaces within the tooth. A cross-section of the incisor is shown in FIG. 7 illustrating the enamel 70, dead tracts 72, dentin 74, pulp 76, and cementum 78. The dentino-enamel (DEJ), dentino-pulp (DPJ), and dentino-cementum (DCJ) junctions are also visible. In addition, a region of dentin containing dead tracts is also present. Results from measurements taken at four different locations through the tooth are presented here. These measurement locations are marked in FIG. 7 as (1), (2), (3), and (4), respectively. In addition, the thickness of each dental hard and soft layer is listed in TABLE 3.

TABLE 3

| Measurement Location | Internal Structure of Tooth in mm | | | | |
|---|---|---|---|---|---|
| 1 | | | Enamel 6.06 | | |
| 2 | | Enamel 0.95 | Dentin 4.76 | Enamel 1.23 | |
| 3 | | Dentin 1.51 | Pulp 0.53 | Dentin 1.3 | Cementum 0.21 |
| 4 | Cementum 0.32 | Dentin 1.13 | Pulp 0.47 | Dentin 0.86 | Cementum 0.48 |

FIGS. 8a-d illustrate the acoustic waveforms determined at the measurement locations shown in FIG. 7, respectively.

Figure 8A:
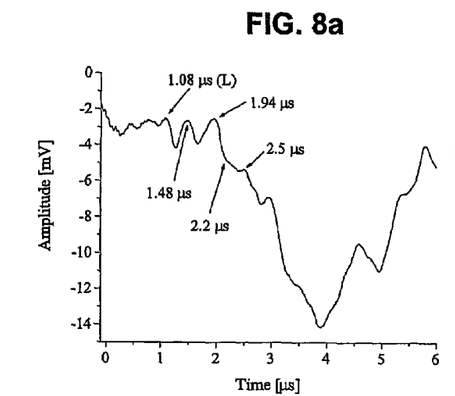
FIG. 8a illustrates an ultrasonic waveform for a human incisor taken in an enamel region.

The first measurement location was taken through the top portion of the tooth and its waveform is illustrated in FIG. 8a. In this region, a straight path across the tooth would only propagate through enamel. The first longitudinal acoustic wave arrival (L) occurs at about 1.08 µs, which is slightly longer than the 0.98 µs expected assuming a longitudinal velocity of 6.25 mm/µs (see TABLE 2). However, as previously discussed, the wave speed is known to vary in enamel due to the anisotropic nature of the elastic properties. The anisotropy is especially pronounced in this region of the tooth since the ultrasonic waves propagate both parallel and perpendicular to the enamel rods. An interesting feature of this waveform is the presence of the two large acoustic wave arrivals at 1.48 µs and 1.98 µs. These arrivals are believed due to acoustic wave scattering from the top surface of the tooth, which is just above the measurement location. This phenomenon illustrates the difficulty in interpreting bulk measurements near interfaces. The acoustic wave arrival at 2.2 µs is very close to the expected wave arrival time of the first shear wave (S). Acoustic wave arrivals at 2.5 µs and later correspond to reflections and scattering from the internal structure of the tooth and do not lend themselves to straightforward interpretation.

Figure 8B:
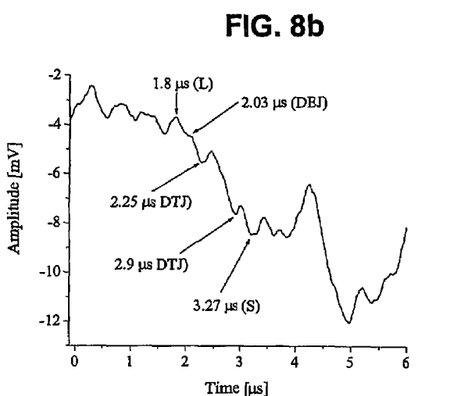
FIG. 8b illustrates an ultrasonic waveform for a human incisor taken in an enamel/amalgam/enamel region.

The second measurement location is approximately four millimeters down from the top of the tooth and its waveform is illustrated in FIG. 8b. In this region, the ultrasonic waves propagate through two DEJs and a region of dead tracts in the dentin. The first longitudinal arrival (L) occurs at about 1.8 µs. This time corresponds to a sudden negative change in slope. Also marked on the waveform is a wave arrival occurring at 2.03 µs (indicated by a positive slope change). This is believed to be due to an additional round trip through the enamel on the left hand side of the dentin caused by reflections at the DEJ. This arrival is more pronounced than in the tooth phantom (FIG. 6b) due to the larger reflection coefficient at the DEJ. The predicted arrival time for this reflection at the DEJ is 1.9 µs. The acoustic wave arrival at 2.25 µs is believed to be due to reflections at the interfaces of the dead tracts. Dead tracts are characterized by the death of odontoblasts, resulting in dentin tubules that contain debris and voids. It is for this reason that dead tracts appear black when teeth are sectioned and viewed by transmitted light. The presence of debris and open spaces in the tubules are expected to significantly affect the mechanical properties of the dentin, resulting in large reflections at the dead tract junctions (DTJ). This difference in mechanical properties contributes to the large acoustic wave arrival (similar to what is seen at the dentino-pulp junction). The DTJ is probably also responsible for the next acoustic wave arrival at 2.9 µs. The final marked wave arrival at 3.27 µs corresponds to the expected arrival time for the shear wave (S) of 3.2 µs. Again, there is expected to be some variation between predicted and measured acoustic wave arrival times, although now the propagation direction is mostly parallel to the orientation of the enamel rods. In this region of the tooth, the dentin tubules run almost perpendicular to the direction of the wave propagation.

Figure 8C:
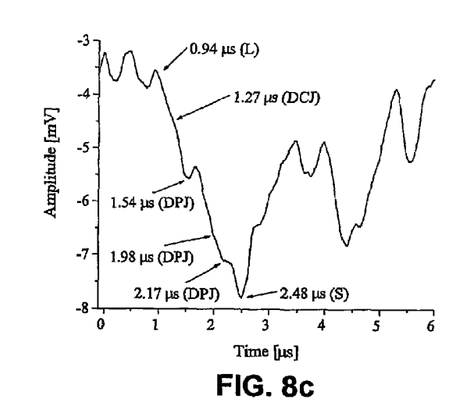
FIG. 8c illustrates an ultrasonic waveform for a human incisor taken in an enamel/dentin/enamel region.

The third measurement location occurs much further down the tooth and its waveform is illustrated in FIG. 8c. In this region, the acoustic wave travels through dentin, pulp, and a small amount of cementum. The mechanical properties (i.e. acoustic wave speeds and density) of cementum are not known. For analysis purposes, it is assumed that the mechanical properties of cementum are similar to those of enamel. Based upon this assumption, the first longitudinal wave arrival is expected at 1.1 µs, which is slightly longer than the measured arrival time of 0.94 µs. This delayed arrival time is attributed to both a degradation in the mechanical properties of the pulp and uncertainty in the mechanical properties of the cementum. A second, faint, arrival is seen at 1.27 µs (marked by the change in slope of the waveform). This arrival coincides with the expected reflection at the DCJ. The next three noticeable features occur at 1.54 µs, 1.98 µs, and 2.17 µs. Due to the amplitude of these wave arrivals, they are believed-to be due to reflections at the DPJ. The next wave arrival at 2.48 µs is very close to that expected for the first shear wave arrival at 2.2 µs and displays the expected sudden change in slope as found with the dentin/pulp/dentin tooth phantom at the shear wave arrival.

Figure 8D:
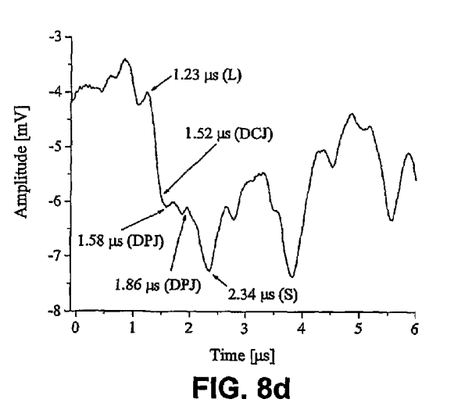
FIG. 8d illustrates an ultrasonic waveform for a human incisor taken in an enamel/dentin/pulp/dentin/enamel region.

The fourth measurement location is near the base of the incisor and its waveform is illustrated in FIG. 8d. At this location, the acoustic wave traveled through two layers of cementum and dentin, as well as a single layer of pulp. The first longitudinal arrival (L) occurs at about 1.23 µs, which is again slower than the expected arrival time of 0.95 µs. The next arrival occurs at 1.52 µs and is attributed to a reflection at a DCJ. The next two reflections occur at 1.58 µs is and 1.86 µs and are due to reflections at the DPJ. Unlike the measurement at the third location, there are only two wave arrivals due to reflections at the DPJ, because the total transit time in the pulp and dentin on the left hand side of the pulp are identical. The final arrival is due to the principal shear wave (S) and occurs at 2.34 µs. As with the longitudinal wave, this arrival time is slower than the predicted time of 1.89 µs and again attributed to degradation of the pulp.

Sources of error should be examined to determine the accuracy of the final results. It has been estimated that the error in making laser ultrasonic measurements is less than 1% when considering phenomena such as acoustic diffraction and timing precision from laser alignment. For measurements on specially prepared samples, an error of 0.08% has been estimated in thickness measurements. For the results illustrated herein, the thickness measurement error is greater since a tooth is very irregular in shape and uncertainties in the exact acoustic path due to possible tilt in the tooth may occur during the measurement. It is more likely that there is a 3-4% error in measuring the thickness of the structures within a tooth (i.e. the enamel, dentin, pulp, and cementum). Another consideration is the determination of the exact arrival time of the first longitudinal wave. As shown in FIGS. 8a-d, the arrival time of the first longitudinal wave is not always clear due to noise in the laser vibrometer signal. However, this does not affect the determination of subsequent wave arrivals. Another source of error is the uncertainty of the exact wave velocities in the various dental hard and soft tissues. Young's modulus in enamel depends on both the orientation of the crystals as well as the volumetric fraction and can vary by over 10%.

Until these factors are better understood, complete characterization of dental enamel will be difficult. However, the problem is greatly simplified when measurements are made in the enamel/dentin region of a tooth. In this region, the crystals of the enamel are predominantly oriented along the direction of the acoustic wave propagation, reducing the uncertainty in the Young's modulus. This allows for more accurate estimates of enamel thickness to be made. The s-shaped tubules in dentin also contribute to uncertainties in the Young's modulus. Again, in certain regions, these tubules are oriented parallel to the direction of the acoustic wave propagation, simplifying the analysis. Even with the uncertainties in moduli, the measurements presented here show that DEJ, DPJ, DCJ, and DTJ are discernible and estimates of the thickness of each of these structures can be made. These estimates are not currently possible using any other known technique. In addition, uncertainties in dental structure thickness do not affect the ability to detect any voids within a tooth.

The application of laser ultrasonics to the in-vitro assessment of the internal structure of teeth has been presented herein and shown to possess significant advantages over prior art work. In laser ultrasonics, a short-pulse laser is used to non-destructively generate broadband, high frequency acoustic waves in the tooth structure. Unlike previous attempts to characterize the internal structure teeth using conventional contact transducers, laser generation of ultrasound requires no special surface preparation. Knowledge of the acoustic wave velocities in and reflection coefficients between the different dental structures allows for the internal structure of the tooth to be reconstructed. Optical detection of the acoustic waves provides a complementary non-contact technique requiring no special surface preparation. Another advantage of optical detection is that the detection footprint can easily be reduced to a few tens of microns, providing high spatial sensitivity in dental characterization.

In the present invention, the dentinoenamel, dentin/pulp, and cementum/dentin interfaces were resolved. The measured acoustic wave arrival times have been shown to generally agree with expected arrival times. The largest source of error in this analysis is likely due to the large variations in the mechanical properties of dental hard tissues. The anisotropic nature of enamel has been well documented. These variations will always make exact determination of the internal structure of a tooth somewhat difficult. However, good estimates of spatial variations in the thicknesses of dental tissues have been shown herein and these measurements have shown the technique of the present invention to be very sensitive to the presence of anomalies in a tooth, such as dead tracts. Moreover, the dentinoenamel, dentino-pulp, and dentino-cementum interfaces as well as dead tracts in the dentin were able to be resolved.

In the following claims, any means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A method of assessing tooth structure using laser based ultrasonics comprising:
   generating ultrasonic acoustic waves using a pulsed laser that emits a beam;
   focusing the beam of the pulsed laser onto a desired area on the surface of a tooth thereby creating ultrasonic acoustic waves within the bulk and on the surface of the tooth structure;
   optically detecting the acoustic waveforms generated within and on the surface of the tooth structure using optical interferometric detection means; and
   processing the detected acoustic waveforms to assess the internal and surface structure of the tooth.

2. The method of claim 1 wherein the pulsed laser is comprised of a short pulse $CO_2$ laser.

3. The method of claim 1 wherein the pulsed laser is comprised of a short pulse laser that operates in region of absorption for the tooth structure.

4. The method of claim 1 wherein the pulsed laser is comprised of a short pulse laser that operates in a region of absorption of a film that is placed on the surface of the tooth.

5. The method of claim 1 wherein the optical interferometric detection means is comprised of a laser vibrometer.

6. The method of claim 1 wherein the optical interferometric detection means is comprised of a Fabry-Perot interferometer.

7. The method of claim 1 wherein the optical interferometric detection means is comprised of a Mach-Zender interferometer.

8. The method of claim 1 wherein the optical interferometric detection means is comprised of a photo-refractive interferometer.

9. The method of claim 1 wherein the optical interferometric detection means is comprised of an intensity feedback interferometer.

10. The method of claim 1 wherein measurements are taken in an epicentral configuration in which the pulsed laser and the optical interferometric detection means are on opposite sides of the tooth.

11. The method of claim 1 wherein measurements are taken in a non-epicentral configuration in which the pulsed laser and the optical interferometric detection means are on opposite sides of the tooth.

12. The method of claim 1 wherein measurements are taken in which the pulsed laser and the optical interferometric detection means are on the same side of the tooth.

13. The method of claim 1 further comprising triggering the detection of the acoustic waveforms within the tooth structure using a high-speed photodetector that samples the output of the pulsed laser.

14. The method of claim 1 wherein said processing step comprises:
   forwarding the acoustic waveforms detected by the optical interferometric detection means to an oscilloscope; and
   analyzing the arrival times and amplitudes of wavefronts within a waveform as presented on the oscilloscope.

15. The method of claim 1 wherein the tooth surface requires no special preparation.

16. The method of claim 15 wherein the beam of the pulsed laser is focused onto the surface of a tooth via a lens apparatus.

17. A method of detecting and processing ultrasonic acoustic waves within and on the surface of a tooth comprising:
   optically detecting the acoustic waveforms within and on the surface of the tooth structure using interferometric detection means; and
   processing the detected acoustic waveforms to assess the internal structure of the tooth.

18. The method of claim 17 wherein the optical interferometric detection means is comprised of a laser vibrometer.

19. The method of claim 17 wherein the optical interferometric detection means is comprised of a Fabry-Perot interferometer.

20. The method of claim 17 wherein the optical interferometric detection means is comprised of a Mach-Zender interferometer.

21. The method of claim 17 wherein the optical interferometric detection means is comprised of a photo-refractive interferometer.

22. The method of claim 17 wherein the optical interferometric detection means is comprised of a intensity feedback interferometer.

23. The method of claim 17 wherein said processing step comprises:
   forwarding the acoustic waveforms detected by the optical interferometric detection means to an oscilloscope; and
   analyzing the arrival times and intensities of wavefronts within a waveform as presented on the oscilloscope.

* * * * *